US012582374B2

(12) United States Patent
Al'Aref et al.

(10) Patent No.: US 12,582,374 B2
(45) Date of Patent: Mar. 24, 2026

(54) PERSONALIZED MOTION-GATED CORONARY CTA SCANNING SYSTEMS AND METHODS

(71) Applicant: BioVentures, LLC, Little Rock, AR (US)

(72) Inventors: Subhi Al'Aref, Little Rock, AR (US); Kedar Jambhekar, Little Rock, AR (US)

(73) Assignee: BioVentures, LLC

( * ) Notice: Subject to any disclaimer, the term of this patent is extended or adjusted under 35 U.S.C. 154(b) by 0 days.

(21) Appl. No.: 18/712,887

(22) PCT Filed: Nov. 30, 2022

(86) PCT No.: PCT/US2022/080685
§ 371 (c)(1),
(2) Date: May 23, 2024

(87) PCT Pub. No.: WO2023/102441
PCT Pub. Date: Jun. 8, 2023

(65) Prior Publication Data
US 2024/0415481 A1    Dec. 19, 2024

Related U.S. Application Data

(60) Provisional application No. 63/284,394, filed on Nov. 30, 2021.

(51) Int. Cl.
*A61B 6/03* (2006.01)
*A61B 6/00* (2006.01)
*A61B 6/50* (2024.01)

(52) U.S. Cl.
CPC .............. *A61B 6/541* (2013.01); *A61B 6/032* (2013.01); *A61B 6/503* (2013.01); *A61B 6/504* (2013.01)

(58) Field of Classification Search
CPC ......... A61B 6/032; A61B 6/503; A61B 6/504; A61B 6/5264; A61B 6/5288; A61B 6/541;
(Continued)

(56) References Cited

U.S. PATENT DOCUMENTS

2004/0081269 A1*  4/2004  Pan ........................ A61B 6/032
                                                            378/4
2005/0249327 A1*  11/2005  Wink ..................... A61B 6/541
                                                            378/8
(Continued)

OTHER PUBLICATIONS

International Search Report and Written Opinion for PCT Application No. PCT/US2022/080685, dated Mar. 9, 2023 (8 Pages).

*Primary Examiner* — Michael J Carey
*Assistant Examiner* — Maria Christina Talty
(74) *Attorney, Agent, or Firm* — Polsinelli PC

(57) ABSTRACT

Disclosed herein are systems and methods for personalized AI-guided motion-gated coronary CTA scanning. The method may include receiving initial CT data from a CT scanner, generating a four-dimensional (4D) computed tomography (CT) image of the heart of the patient from the initial CT data, identifying mechanical movement of the heart of the patient and an initial timeframe when the myocardium of the heart of the patient is in a target position, and using the mechanical movement of the heart of the patient and the initial timeframe to predict a subsequent timeframe when the heart of the patient will be in the target position. The system may include at least one processor and a memory storing instructions that, when executed by the at least one processor, causes the at least one processor to perform any or all of the method steps, operations, or processes described in the present disclosure.

20 Claims, 3 Drawing Sheets

(58) Field of Classification Search
 CPC ................... A61B 6/542; G06N 20/00; G06T
 2207/10076; G06T 7/0016; G06T 7/20
 See application file for complete search history.

(56) References Cited

U.S. PATENT DOCUMENTS

| | | | |
|---|---|---|---|
| 2008/0285819 A1 | 11/2008 | Konofagou et al. | |
| 2012/0078097 A1* | 3/2012 | Wang ................... | A61B 8/0883 |
| | | | 600/437 |
| 2015/0305692 A1* | 10/2015 | Klahr ................... | A61N 5/1039 |
| | | | 600/425 |
| 2020/0163639 A1* | 5/2020 | De Man .................... | G06T 7/20 |
| 2020/0250826 A1* | 8/2020 | Cohen Maimon ..... | G16H 30/20 |
| 2021/0125331 A1* | 4/2021 | Sun ...................... | G06N 3/0464 |

* cited by examiner

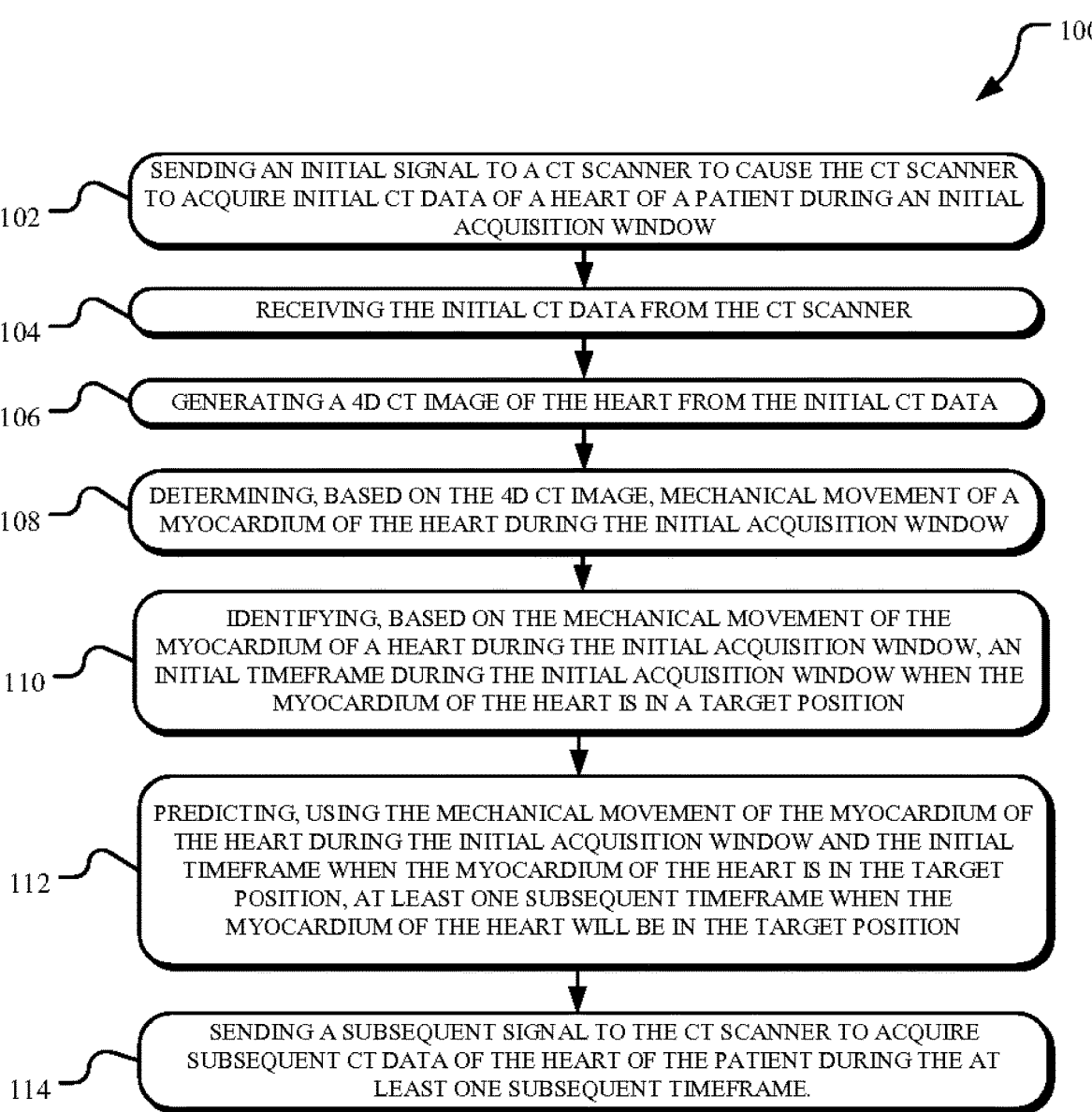

100

102 — SENDING AN INITIAL SIGNAL TO A CT SCANNER TO CAUSE THE CT SCANNER TO ACQUIRE INITIAL CT DATA OF A HEART OF A PATIENT DURING AN INITIAL ACQUISITION WINDOW

104 — RECEIVING THE INITIAL CT DATA FROM THE CT SCANNER

106 — GENERATING A 4D CT IMAGE OF THE HEART FROM THE INITIAL CT DATA

108 — DETERMINING, BASED ON THE 4D CT IMAGE, MECHANICAL MOVEMENT OF A MYOCARDIUM OF THE HEART DURING THE INITIAL ACQUISITION WINDOW

110 — IDENTIFYING, BASED ON THE MECHANICAL MOVEMENT OF THE MYOCARDIUM OF A HEART DURING THE INITIAL ACQUISITION WINDOW, AN INITIAL TIMEFRAME DURING THE INITIAL ACQUISITION WINDOW WHEN THE MYOCARDIUM OF THE HEART IS IN A TARGET POSITION

112 — PREDICTING, USING THE MECHANICAL MOVEMENT OF THE MYOCARDIUM OF THE HEART DURING THE INITIAL ACQUISITION WINDOW AND THE INITIAL TIMEFRAME WHEN THE MYOCARDIUM OF THE HEART IS IN THE TARGET POSITION, AT LEAST ONE SUBSEQUENT TIMEFRAME WHEN THE MYOCARDIUM OF THE HEART WILL BE IN THE TARGET POSITION

114 — SENDING A SUBSEQUENT SIGNAL TO THE CT SCANNER TO ACQUIRE SUBSEQUENT CT DATA OF THE HEART OF THE PATIENT DURING THE AT LEAST ONE SUBSEQUENT TIMEFRAME.

*FIG. 1*

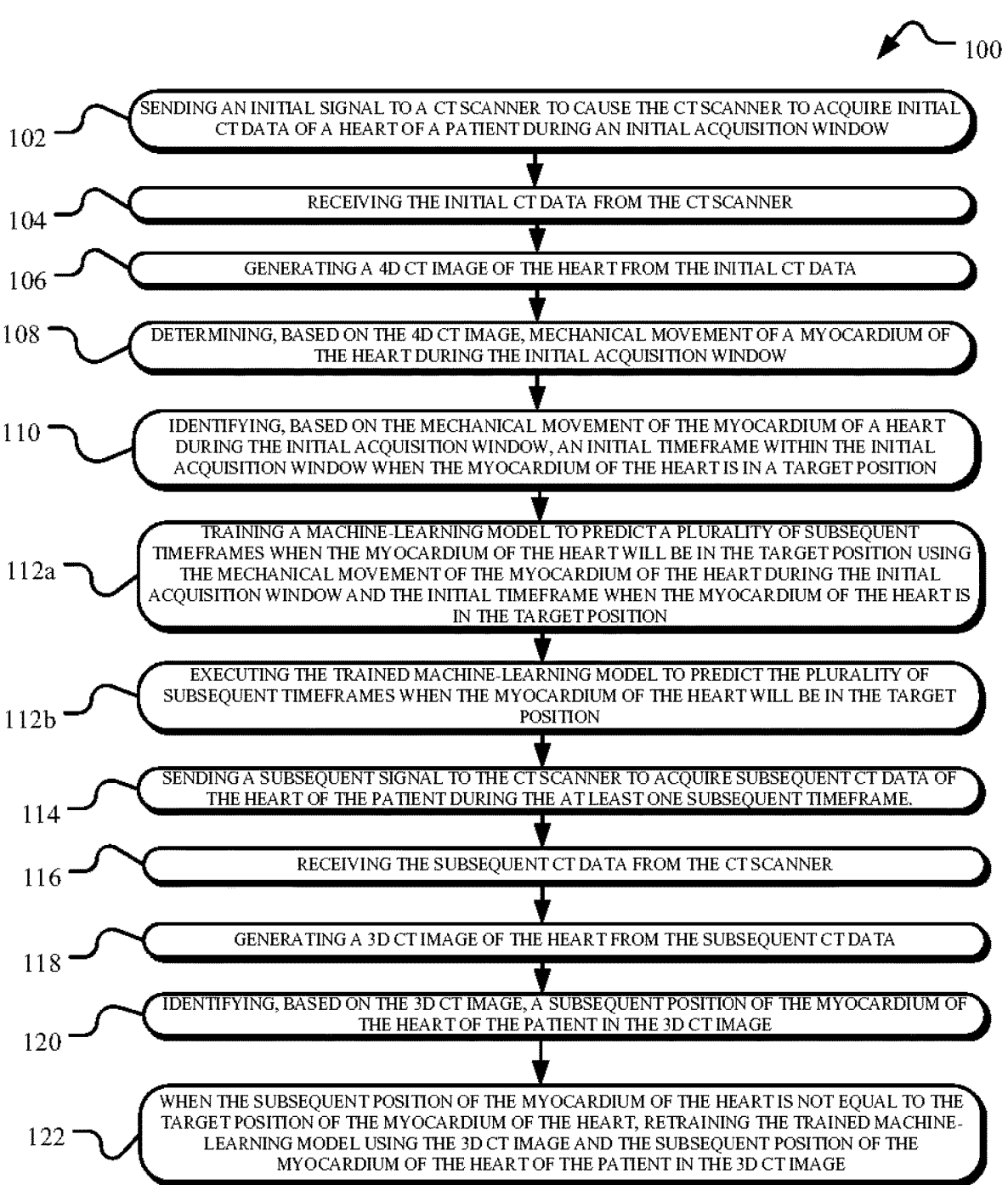

100

102 — SENDING AN INITIAL SIGNAL TO A CT SCANNER TO CAUSE THE CT SCANNER TO ACQUIRE INITIAL CT DATA OF A HEART OF A PATIENT DURING AN INITIAL ACQUISITION WINDOW

104 — RECEIVING THE INITIAL CT DATA FROM THE CT SCANNER

106 — GENERATING A 4D CT IMAGE OF THE HEART FROM THE INITIAL CT DATA

108 — DETERMINING, BASED ON THE 4D CT IMAGE, MECHANICAL MOVEMENT OF A MYOCARDIUM OF THE HEART DURING THE INITIAL ACQUISITION WINDOW

110 — IDENTIFYING, BASED ON THE MECHANICAL MOVEMENT OF THE MYOCARDIUM OF A HEART DURING THE INITIAL ACQUISITION WINDOW, AN INITIAL TIMEFRAME WITHIN THE INITIAL ACQUISITION WINDOW WHEN THE MYOCARDIUM OF THE HEART IS IN A TARGET POSITION

112a — TRAINING A MACHINE-LEARNING MODEL TO PREDICT A PLURALITY OF SUBSEQUENT TIMEFRAMES WHEN THE MYOCARDIUM OF THE HEART WILL BE IN THE TARGET POSITION USING THE MECHANICAL MOVEMENT OF THE MYOCARDIUM OF THE HEART DURING THE INITIAL ACQUISITION WINDOW AND THE INITIAL TIMEFRAME WHEN THE MYOCARDIUM OF THE HEART IS IN THE TARGET POSITION

112b — EXECUTING THE TRAINED MACHINE-LEARNING MODEL TO PREDICT THE PLURALITY OF SUBSEQUENT TIMEFRAMES WHEN THE MYOCARDIUM OF THE HEART WILL BE IN THE TARGET POSITION

114 — SENDING A SUBSEQUENT SIGNAL TO THE CT SCANNER TO ACQUIRE SUBSEQUENT CT DATA OF THE HEART OF THE PATIENT DURING THE AT LEAST ONE SUBSEQUENT TIMEFRAME.

116 — RECEIVING THE SUBSEQUENT CT DATA FROM THE CT SCANNER

118 — GENERATING A 3D CT IMAGE OF THE HEART FROM THE SUBSEQUENT CT DATA

120 — IDENTIFYING, BASED ON THE 3D CT IMAGE, A SUBSEQUENT POSITION OF THE MYOCARDIUM OF THE HEART OF THE PATIENT IN THE 3D CT IMAGE

122 — WHEN THE SUBSEQUENT POSITION OF THE MYOCARDIUM OF THE HEART IS NOT EQUAL TO THE TARGET POSITION OF THE MYOCARDIUM OF THE HEART, RETRAINING THE TRAINED MACHINE-LEARNING MODEL USING THE 3D CT IMAGE AND THE SUBSEQUENT POSITION OF THE MYOCARDIUM OF THE HEART OF THE PATIENT IN THE 3D CT IMAGE

*FIG. 2*

PERSONALIZED MOTION-GATED CORONARY CTA SCANNING SYSTEMS AND METHODS

CROSS-REFERENCE TO RELATED APPLICATION

This application claims priority to International Application No. PCT/US2022/080685, filed Nov. 30, 2022, which claims priority to U.S. Provisional Application No. 63/284,394, filed Nov. 30, 2021, the contents of which are entirely incorporated by reference herein.

FIELD

The present disclosure relates to systems and methods for motion-gated coronary computed tomography angiography (coronary CTA) scanning. More specifically, the disclosure relates to personalized motion-gated coronary CTA scanning using four-dimensional (4D) computed tomography (CT) images.

BACKGROUND

Coronary artery disease (CAD) is the leading cause of death in the United States for both men and women and accounts for approximately 360,000 deaths annually. As such, assessing for atherosclerotic plaque and the occurrence of myocardial ischemia is crucial to diagnosing and treating CAD. Although coronary computed tomography angiography (coronary CTA) is a powerful tool for assessing CAD, current methods and systems for performing coronary CTAs can be expensive, time consuming, and difficult or impossible to perform on some patients. Imaging objects that are in motion, such as the heart, requires the use of techniques to reduce motion-induced artifacts.

Typically, coronary CTAs are performed using electrocardiogram-gating (ECG-gating), which involves using electrocardiography to infer the mechanical systolic and diastolic phases of the heart and synchronizing coronary CTA image acquisition with the diastolic phase to minimize motion of the heart. This technique helps to decrease the presence of motion artifacts but has several limitations. For example, to minimize coronary motion and maximize the diastolic phase, the heart rate must be lowered to 55 to 65 beats per minute and the patient's heart must be in normal sinus rhythm. This requires significant cost, time, and effort in terms of administering medications to lower the heart rate of the patient, pre-scan preparation and monitoring, and management of complications, and prohibits scanning patients who are not in normal sinus rhythm. Additionally, a significant portion of patients are unable to achieve the goal heart rate of 55 to 65 beats per minute, for example, patients with anxiety, dehydration, or heart failure.

Therefore, there is a need for systems and methods for gating coronary CTA scanning that remedy the deficiencies of the prior art.

SUMMARY

The present disclosure provides systems and methods for personalized motion-gated coronary computed tomography angiography (coronary CTA) scanning using four-dimensional (4D) computed tomography (CT) images, as well as systems and methods for personalized artificial-intelligence (AI) guided motion-gated coronary CTA scanning using 4D CT images.

In some aspects, the techniques described herein relate to a computer-implemented method, including: sending an initial signal to a CT scanner to acquire initial CT data of a heart of a patient during an initial acquisition window; receiving the initial CT data from the CT scanner; generating a four-dimensional (4D) CT image of the heart from the initial CT data; determining, based on the 4D CT image, mechanical movement of a myocardium of the heart during the initial acquisition window; identifying, based on the mechanical movement of the myocardium of the heart during the initial acquisition window, an initial timeframe during the initial acquisition window when the myocardium of the heart is in a target position; predicting, using the mechanical movement of the myocardium of the heart during the initial acquisition window and the initial timeframe within the initial acquisition window when the myocardium of the heart is in the target position, a plurality of subsequent timeframes when the myocardium of the heart will be in the target position; sending a subsequent signal to the CT scanner to acquire subsequent CT data of the heart of the patient during the plurality of subsequent timeframes.

In some aspects, the techniques described herein relate to a computer-implemented method, wherein the initial acquisition window is a length of time equal to at least one full cardiac cycle of the patient.

In some aspects, the techniques described herein relate to a computer-implemented method, wherein the initial acquisition window is 0.5-10 seconds.

In some aspects, the techniques described herein relate to a computer-implemented method, wherein the initial acquisition window is 0.5-2 seconds.

In some aspects, the techniques described herein relate to a computer-implemented method, wherein the heart is in the target position when the myocardium of the heart is closest to a detector of the CT scanner.

In some aspects, the techniques described herein relate to a computer-implemented method, wherein generating a 4D CT image of the heart from the initial CT data includes generating the 4D CT image in real time.

In some aspects, the techniques described herein relate to a computer-implemented method, further including generating an alarm or notification to indicate when to administer coronary CTA contrast to the patient.

In some aspects, the techniques described herein relate to a computer-implemented method, wherein the alarm or notification is generated after sending the initial signal to the CT scanner and prior to sending the subsequent signal to the CT scanner.

In some aspects, the techniques described herein relate to a computer-implemented method, further including: receiving the subsequent CT data; and generating a 3D CT image of the heart from the subsequent CT data.

In some aspects, the techniques described herein relate to a computer-implemented method, wherein generating the 3D CT image of the heart from the subsequent CT data includes generating the 3D CT image in real time.

In some aspects, the techniques described herein relate to a computer-implemented method, wherein predicting the plurality of subsequent timeframes when the myocardium of the heart will be in the target position includes: training a machine-learning model to predict the plurality of subsequent timeframes when the myocardium of the heart will be in the target position using the mechanical movement of the myocardium of the heart during the initial acquisition window and the initial timeframe within the initial acquisition window when the myocardium of the heart is in the target position; and executing the trained machine-learning model to predict the plurality of subsequent timeframes when the myocardium of the heart will be in the target position.

In some aspects, the techniques described herein relate to a computer-implemented method, further including: identifying, based on the 3D CT image, a subsequent position of the myocardium of the heart of the patient in the 3D CT image; and when the subsequent position of the myocardium of the heart is not equal to the target position of the myocardium of the heart, retraining the trained machine-learning model using the 3D CT image and the subsequent position of the myocardium of the heart of the patient in the 3D CT image.

In some aspects, the techniques described herein relate to a computer-implemented method, further including: identifying, based on the 4D CT image, a heart arrythmia of the patient, wherein training the machine-learning model to predict the at plurality of subsequent timeframes further includes using the heart arrythmia of the patient.

In some aspects, the techniques described herein relate to a computer-implemented method, wherein the subsequent CT data includes CT images of a plurality of segments of the myocardium corresponding to a coronary artery tree of the heart, and wherein sending the subsequent signal to the CT scanner to acquire the subsequent CT data of the heart of the patient during the plurality of subsequent timeframes includes sending the subsequent signal to the CT scanner to acquire the CT images of each of the plurality of segments of the myocardium until an entirety of the coronary artery tree of the heart is imaged.

In some aspects, the techniques described herein relate to a system, including a at least one processor and a memory storing instructions that, when executed by the at least one processor, cause the at least one processor to: send an initial signal to a computed tomography (CT) scanner to cause the CT scanner to acquire initial CT data of a heart of a patient during an initial acquisition window, the initial acquisition window being a length of time equal to one or more cardiac cycles of the heart of the patient; receive the initial CT data; generate a four-dimensional (4D) CT image from the initial CT data; determine, based on the 4D CT image, mechanical movement of a myocardium of the heart during the initial acquisition window; identify, based on the mechanical movement of the myocardium of the heart during the initial acquisition window, an initial timeframe during each of the one or more cardiac cycles when the myocardium of the heart is in a target position; predict, based on the mechanical movement of the myocardium of the heart during the initial acquisition window and the initial timeframe during each of the one or more cardiac cycles when the myocardium of the heart is in the target position, a plurality of subsequent timeframes when the myocardium of the heart will be in the target position; and send a subsequent signal to the CT scanner to cause the CT scanner to acquire subsequent CT data at the plurality of subsequent timeframes.

In some aspects, the techniques described herein relate to a system, wherein the initial acquisition window is 0.5-10 seconds.

In some aspects, the techniques described herein relate to a system, wherein the initial acquisition window is 0.5-2 seconds.

In some aspects, the techniques described herein relate to a system, wherein the heart is in the target position when the myocardium of the heart is closest to a detector of the CT scanner.

In some aspects, the techniques described herein relate to a system, wherein the instructions, when executed by the at least one processor, further cause the at least one processor to generate the 4D CT image from the initial CT data in real time.

In some aspects, the techniques described herein relate to a system, wherein the instructions, when executed by the at least one processor, further cause the at least one processor to generate an alarm or notification at the system, to indicate when to administer coronary CTA contrast to the patient.

In some aspects, the techniques described herein relate to a system, wherein the instructions, when executed by the at least one processor, cause the at least one processor to generate the alarm or notification after sending the initial signal to the CT scanner and prior to sending the subsequent signal to the CT scanner.

In some aspects, the techniques described herein relate to a system, wherein the instructions, when executed by the at least one processor, further cause the at least one processor to: receive the subsequent CT data; and generate a 3D CT image from the subsequent CT data.

In some aspects, the techniques described herein relate to a system, wherein the instructions, when executed by the at least one processor, further cause the at least one processor to generate the 3D CT image from the subsequent CT data in real time.

In some aspects, the techniques described herein relate to a system, wherein the instructions, when executed by the at least one processor, further cause the at least one processor to: train a machine-learning model to predict the plurality of subsequent timeframes when the myocardium of the heart will be in the target position using the mechanical movement of the myocardium of the heart during the initial acquisition window and the initial timeframe within the initial acquisition window when the myocardium of the heart is in the target position; and execute the trained machine-learning model to predict the plurality of subsequent timeframes when the myocardium of the heart will be in the target position.

In some aspects, the techniques described herein relate to a system, wherein the instructions, when executed by the at least one processor, further cause the at least one processor to: identify, based on the 3D CT image, a subsequent position of the myocardium of the heart of the patient in the 3D CT image; determine, based on the 3D CT image, that the subsequent position of the myocardium of the heart is not equal to the target position of the myocardium of the heart; and when the subsequent position of the myocardium of the heart is not equal to the target position of the myocardium of the heart, retrain the trained machine-learning model using the 3D CT image and the subsequent position of the myocardium of the heart of the patient in the 3D CT image.

In some aspects, the techniques described herein relate to a system, wherein the instructions, when executed by the at least one processor, further cause the at least one processor to: identify, based on the 4D CT image, a heart arrythmia of the patient, wherein training the machine-learning model to predict the at plurality of subsequent timeframes further includes using the heart arrythmia of the patient.

In some aspects, the techniques described herein relate to a system, wherein the subsequent CT data includes CT images of a plurality of segments of the myocardium corresponding to a coronary artery tree of the heart, and wherein the instructions, when executed by the at least one processor, cause the at least one processor to send the subsequent signal to the CT scanner to acquire the subsequent CT images of each of the plurality of segments of the myocardium during the plurality of subsequent timeframes until an entirety of the coronary artery tree of the heart is imaged.

Other aspects and iterations of the invention are described more thoroughly below.

BRIEF DESCRIPTION OF THE DRAWINGS

The description will be more fully understood with reference to the following figures, which are presented as various embodiments of the disclosure and should not be construed as a complete recitation of the scope of the disclosure. It is noted that, for purposes of illustrative clarity, certain elements in various drawings may not be drawn to scale. Understanding that these drawings depict only exemplary embodiments of the disclosure and are not therefore to be considered to be limiting of its scope, the principles herein are described and explained with additional specificity and detail through the use of the accompanying drawings in which:

FIG. 1 is a flow chart of an example method for performing personalized motion-gated coronary computed tomography angiography (CTA) scanning using four-dimensional (4D) computed tomography (CT) images;

FIG. 2 Is a flow chart of the method of FIG. 1, showing additional steps of the method for performing personalized motion-gated coronary CTA scanning using 4D CT images.

Reference characters indicate corresponding elements among the views of the drawings. The headings used in the figures do not limit the scope of the claims.

DETAILED DESCRIPTION

Figure 3:
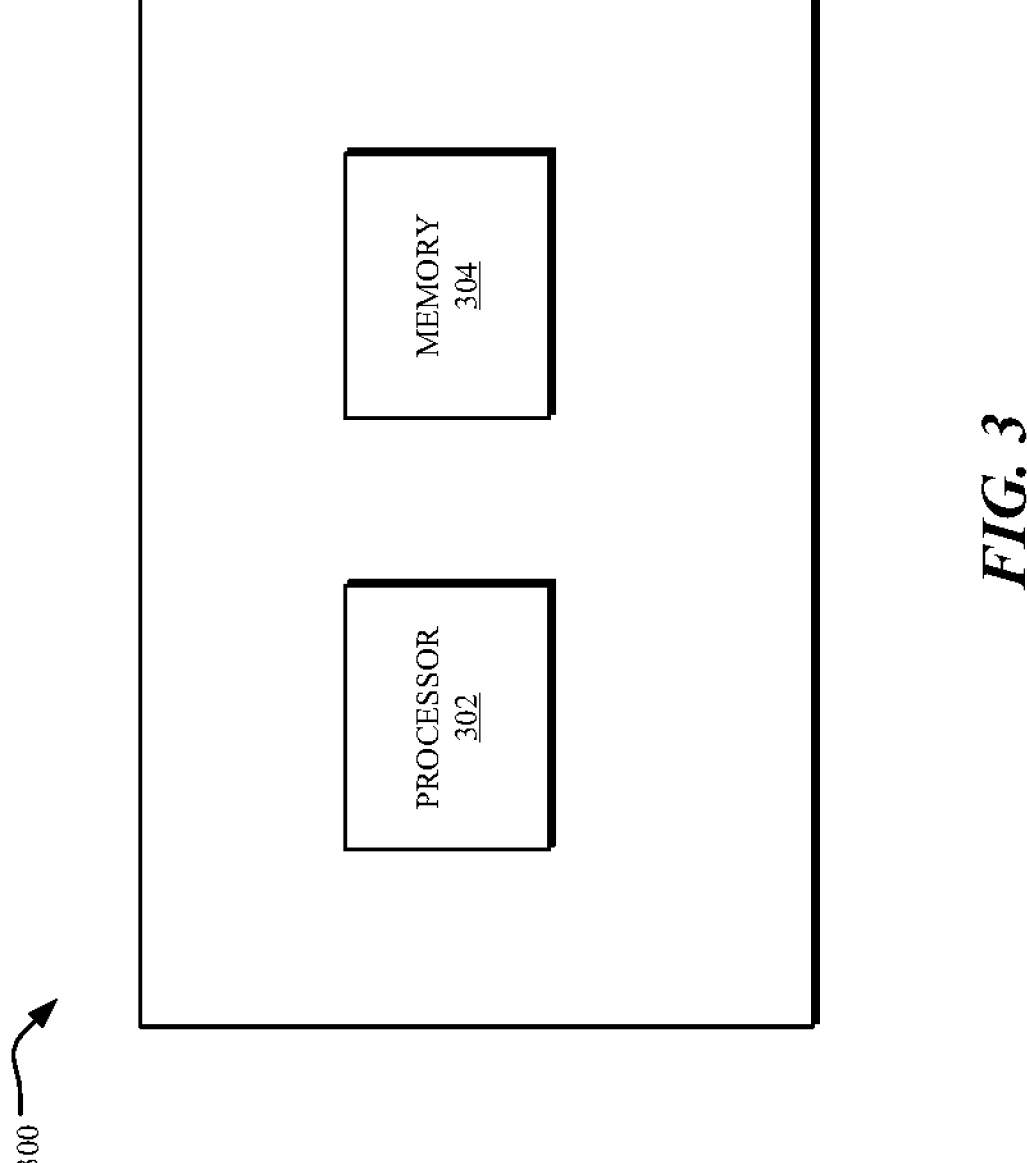
FIG. 3 is a block diagram of an example system for a personalized motion-gated coronary CTA scanning using 4D CT images.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described avoid obscuring the description. References to one or an embodiment in the present disclosure can be references to the same embodiment or any embodiment; and, such references mean at least one of the embodiments.

Reference to "one embodiment", "an embodiment", or "an aspect" means that a particular feature, structure, or characteristic described in connection with the embodiment is included in at least one embodiment of the disclosure. The appearances of the phrase "in one embodiment" or "in one aspect" in various places in the specification are not necessarily all referring to the same embodiment, nor are separate or alternative embodiments mutually exclusive of other embodiments. Moreover, various features are described which may be exhibited by some embodiments and not by others.

Unless specifically stated otherwise, it is appreciated that throughout this specification discussions utilizing terms such as "processing," "computing," "calculating," "determining," "identifying," "generating," or the like refer to actions or processes of a computing device, such as one or more computers or a similar electronic computing device or devices, that manipulate or transform data represented as physical electronic or magnetic quantities within memories, registers, or other information storage devices, transmission devices, or media devices of the computing platform. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited.

As used herein, CT data refers to time-stamped X-ray projections detected by a detector of the CT scanner, as commonly known in the art. The term "CT data" refers to data acquired by a CT scanner during image acquisition, including X-rays detected by X-ray detectors of the CT scanner, time-stamp data associated with the x-rays, and may include personalized patient data, such as identifying information.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Provided herein are systems and methods for personalized motion-gated coronary computed tomography angiography (CTA) scanning using four-dimensional (4D) computed tomography (CT) images, including, but not limited to personalized artificial intelligence (AI) guided motion-gated coronary CTA scanning using 4D CT images. Assessing atherosclerotic plaque and the occurrence of myocardial ischemia is crucial to diagnosing and treating CAD. The systems and methods provided herein improve current techniques for performing coronary computed tomography angiography (coronary CTA) by synchronizing data acquisition with the mechanical motion of the heart to generate CT images that are substantially free of motion-induced artifacts.

The systems and methods of the present disclosure use 4D CT scans of a patient to monitor mechanical motion of the myocardium of the heart of the patient and determine an initial timeframe when the myocardium of the heart is in a target position, indicating a quiescent phase of the cardiac cycle that is ideal for coronary CTA image acquisition. The systems and methods use this data to predict subsequent timeframes when the myocardium of the heart of the patient will be in the target position and signal to a CT scanner to acquire images during the subsequent timeframes. This technique is personalized to each patient and is advantageous because it synchronizes coronary CTA image acquisition with the mechanical motion of the heart, to more consistently identify the quiescent phase of the cardiac cycle, as compared to ECG-gating, which only infers mechanical motion of the heart. Thus, the systems and methods of the present disclosure minimize and/or eliminate the need for medications and pre-scan preparation to slow the patient's heart and decrease the amount of image processing needed to remove motion-induced artifacts.

Further, in some aspects the systems and methods of the present disclosure use built-in AI algorithms and machine-learning to train, retrain, and optimize image acquisition and to develop tracking methods to allow coronary CTAs to be performed on patients with arrythmias, such as tachycardia.

Thus, the systems and methods of the present disclosure overcome the deficiencies of the prior art by making coronary CTAs accessible to more patients and decreasing costs and time required to perform coronary CTAs.

FIG. 1 is a flow chart of an example method 100 for performing personalized AI-guided motion-gated coronary CTA scanning using four-dimensional (4D) CT images according to aspects of the present disclosure.

Any of the steps, operations, or processes of the methods, such as method 100, described herein may be performed or implemented with one or more hardware or software modules, alone or in combination with other devices. In some examples, a software module can be implemented with a computer-readable medium storing instructions, such as computer program code, which can be executed by a general-purpose computer, special purpose computer, or at least one processor for performing any or all of the steps, operations, or processes described.

At step 102, an initial signal may be sent to a CT scanner to cause the CT scanner to acquire initial CT data of a heart of a patient during an initial acquisition window.

In some instances, the initial acquisition window may be a length of time equal to at least one full cardiac cycle of the patient. For example, the initial acquisition window may be 0.5-2 seconds or 0.5-10 seconds.

At step 104, the method 100 may include receiving the initial CT data from the CT scanner. For example, the initial CT data may be received at a general-purpose computer, special purpose computer, or at least one processor capable of performing the method 100 of the present disclosure.

At step 106, a 4D CT image of the heart of the patient may be generated from the initial CT data. Generating a CT image, as used herein, refers to reconstructing the CT data received from the CT scanner into a 3D volume or 3D CT image. Further, generating a 4D CT image refers to reconstructing 3D CT images from CT data obtained over a period of time. 4D CT imaging is a commonly imaging method using to view and analyze moving structures, such as the heart and lungs. In some instances, the 4D CT image may be generated from the initial CT data in real time.

At step 108, mechanical movement of a myocardium of the heart of the patient during the initial acquisition window may be determined, based on the 4D CT image. Determining the mechanical movement of the myocardium of the heart of the patient during the initial acquisition window involves analyzing the location and position of the myocardium of the heart over time.

At step 110, the mechanical movement of the myocardium of the heart of the patient may be used to identify an initial timeframe, within the initial acquisition window, when the myocardium of the heart is in a target position. For example, the 4D CT image may be time stamped and the mechanical movement of the heart of the patient (i.e., the location and position of the heart) may be analyzed in each frame of the 4D CT to determine a start time and a stop time, between which, the heart is in the target position. The initial timeframe is defined between the start time and the stop time.

The target position corresponds to a quiescent phase of the cardiac cycle of the heart, when motion of the heart is reduced. In the cardiac cycle of the heart, the quiescent phase is when the heart is in diastole and is filling with blood. In some instances, a distance of the myocardium of the heart may serve as an indicator that the heart is in diastole. For example, in such instances, identifying the initial timeframe when the myocardium of the heart is in the target position may comprise identifying the initial timeframe when the myocardium of the heart is closest to a detector of the CT scanner.

At step 112, the mechanical movement of the myocardium of the heart during the initial acquisition window and the initial timeframe within the initial acquisition window when the myocardium of the heart is in the target position is used to predict a plurality of subsequent timeframes when the myocardium of the heart will be in the target position.

At step 114, at least one subsequent signal is sent to the CT scanner to acquire subsequent CT data of the heart of the patient during the at least one subsequent timeframe. Acquiring the subsequent CT data may comprise performing a coronary CTA scan on the heart of the patient.

In some instances, the subsequent CT data may comprise CT images of a plurality of segments of the myocardium corresponding to a coronary artery tree of the heart of the patient. In such instances, sending the subsequent signal to the CT scanner to acquire the subsequent CT data of the heart of the patient during the plurality of subsequent timeframes comprises sending the subsequent signal to the CT scanner to acquire the CT images of each of the plurality of segments of the myocardium during the plurality of subsequent timeframes until an entirety of the coronary artery tree of the heart is imaged. The coronary arteries of the heart sit on top of the myocardium. Thus, the present disclosure provides systems and methods for obtaining images of the coronary artery tree by using mechanical motion of the heart to determine the target position and image the coronary arteries when they are in the target position, i.e., in a phase of minimal motion. This is advantageous because it allows coronary CTAs to be performed for patients with faster heartrates than current systems and methods.

In some instances, the computer-implemented method further comprises AI and machine-learning aspects. For example, FIG. 2. is a flow chart of the method of FIG. 1, showing additional steps of the method 100 for performing personalized motion-gated coronary CTA scanning using four-dimensional (4D) CT images, incorporating AI and machine-learning aspects. As shown in FIG. 2, step 112, predicting the at least one subsequent timeframe when the myocardium of the heart will be in the target position may comprise: step 112*a*, training a machine-learning model to predict the at least one subsequent timeframe when the myocardium of the heart will be in the target position using the mechanical movement of the myocardium of the heart during the initial acquisition window and the initial timeframe within the initial acquisition window when the myocardium of the heart is in the target position; and step 112*b*, executing the trained machine-learning model to predict the at least one subsequent timeframe when the myocardium of the heart will be in the target position.

In some instances, the computer-implemented method 100 incorporating AI and machine-learning aspects may further comprise, at step 116, receiving the subsequent CT data and, at step 118, generating a 3D CT image of the heart from the subsequent data. In some instances, the 3D CT image of the heart may be generated in real time.

In some instances, the computer-implemented method may further comprise, at step 120, identifying, based on the 3D CT image, a subsequent position of the myocardium of the heart of the patient in the 3D CT image.

In such instances, the computer-implemented method may further comprise, at step 122, retraining the trained machine-learning model using the 3D CT image and the subsequent position of the myocardium of the heart when the subsequent position of the myocardium of the heart is not equal to the target position of the myocardium of the heart.

In some instances, the computer-implemented method may further comprise identifying a heart arrythmia of a patient based on the 4D CT image and training the machine-learning model to predict the at least one subsequent time-frame may further comprise using the identified heart arrythmia of the patient.

In some instances, the computer-implemented method may further comprise storing the initial CT data, the 4D CT image, the target position, and the initial timeframe in memory of a computing device.

In some instances, the computer-implemented method may further comprise generating an alarm or notification to indicate when the administer coronary CTA contrast to the patient. In such instances, the alarm or notification may be generated after sending the initial signal to the CT scanner and prior to sending the subsequent signal to the CT scanner.

FIG. 3. illustrates a system 300 for performing personalized motion-gated coronary CTA scanning using four-dimensional (4D) CT images and/or personalized AI-guided motion-gated coronary CTA scanning using four-dimensional (4D) CT images according to aspects of the present disclosure. The system 300 may include at least one processor 302 and a memory 304 storing instructions.

The system 300 may be capable of performing any or all of the method steps, operations, or processes described in the present disclosure. The system 300 may be constructed for the required purposes, and/or it may comprise a general-purpose computing device selectively activated or reconfigured by a computer program or algorithm stored in the memory 304. The memory 304 may be or include a non-transitory, tangible computer readable storage medium, or any type of media suitable for storing electronic instructions.

The memory 304 may include, for example, instructions and data which cause or otherwise configure a general-purpose computer, special purpose computer, or a processing device, such as the at least one processor 302, to perform a certain function or group of functions. Portions of computer resources used can be accessible over a network. The computer-executable instructions may be, for example, binaries, intermediate format instructions such as assembly language, firmware, source code, etc. The instructions may include an AI algorithm that implements machine-learning models to execute perform any or all of the method steps, operations, or processes described in the present disclosure.

The at least one processor 302, may include a single processor or multiple processors, such as, but not limited to, one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A processor may be a microprocessor; conventional processor, controller, micro-controller, state machine, or the like. A processor may also be implemented as a combination of computing components (e.g., a combination of a DSP and a microprocessor, a plurality of microprocessors, one or more microprocessors in conjunction with a DSP core, or any other such configuration). Accordingly, the term "processor," as used herein may refer to any of the foregoing structure, any combination of the foregoing structure, or any other structure or apparatus suitable for implementation of the techniques described herein. Functionality described herein also can be embodied in peripherals or add-in cards. Such functionality can also be implemented on a circuit board among different chips or different processes executing in a single device, by way of further example.

The instructions, when executed by the at least one processor 302, may cause the at least one processor to perform any or all of the method steps, operations, or processes described in the present disclosure.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the present disclosure. Accordingly, the above description should not be taken as limiting the scope of the disclosure.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A computer-implemented method, comprising:
   sending an initial signal to a computed tomography (CT) scanner to acquire initial CT data of a heart of a patient during an initial acquisition window;
   receiving the initial CT data from the CT scanner;
   generating a four-dimensional (4D) CT image of the heart from the initial CT data;
   determining, based on the 4D CT image, mechanical movement of a myocardium of the heart during the initial acquisition window;
   identifying, based on the mechanical movement of the myocardium of the heart during the initial acquisition window, an initial timeframe during the initial acquisition window when the myocardium of the heart is in a target position;
   predicting, using the mechanical movement of the myocardium of the heart during the initial acquisition window and the initial timeframe within the initial acquisition window when the myocardium of the heart is in the target position, a plurality of subsequent timeframes when the myocardium of the heart will be in the target position, wherein the plurality of subsequent timeframes are updated in real time; and

sending a subsequent signal to the CT scanner to acquire subsequent CT data of the heart of the patient during the plurality of subsequent timeframes.

2. The computer-implemented method of claim 1, wherein the initial acquisition window is a length of time equal to at least one full cardiac cycle of the patient.

3. The computer-implemented method of claim 1, wherein the initial acquisition window is 0.5-10 seconds.

4. The computer-implemented method of claim 1, wherein the heart is in the target position when the myocardium of the heart is closest to a detector of the CT scanner.

5. The computer-implemented method of claim 1, wherein generating the 4D CT image of the heart from the initial CT data comprises generating the 4D CT image in real time.

6. The computer-implemented method of claim 1, further comprising generating an alarm or notification to indicate when to administer coronary CTA (computed tomography angiography) contrast to the patient, wherein the alarm or notification is generated after sending the initial signal to the CT scanner and prior to sending the subsequent signal to the CT scanner.

7. The computer-implemented method of claim 1, further comprising:

receiving the subsequent CT data from the CT scanner; and generating a 3D (three-dimensional) CT image of the heart from the subsequent CT data in real time.

8. The computer-implemented method of claim 7, wherein predicting the plurality of subsequent timeframes when the myocardium of the heart will be in the target position includes:

training a machine-learning model to predict the plurality of subsequent timeframes when the myocardium of the heart will be in the target position using the mechanical movement of the myocardium of the heart during the initial acquisition window and the initial timeframe within the initial acquisition window when the myocardium of the heart is in the target position; and executing the trained machine-learning model to predict the plurality of subsequent timeframes when the myocardium of the heart will be in the target position.

9. The computer-implemented method of claim 8, further comprising:

identifying, based on the 3D CT image, a subsequent position of the myocardium of the heart of the patient in the 3D CT image; and when the subsequent position of the myocardium of the heart is not equal to the target position of the myocardium of the heart, retraining the trained machine-learning model using the 3D CT image and the subsequent position of the myocardium of the heart of the patient in the 3D CT image.

10. The computer-implemented method of claim 9, further comprising:

identifying, based on the 4D CT image, a heart arrhythmia of the patient, wherein training the machine-learning model to predict the at the plurality of subsequent timeframes further comprises using the heart arrhythmia of the patient.

11. The computer-implemented method of claim 1, wherein the subsequent CT data comprises CT images of a plurality of segments of the myocardium corresponding to a coronary artery tree of the heart, and wherein sending the subsequent signal to the CT scanner to acquire the subsequent CT data of the heart of the patient during the plurality of subsequent timeframes comprises sending the subsequent signal to the CT scanner to acquire the CT images of each of the plurality of segments of the myocardium until an entirety of the coronary artery tree of the heart is imaged.

12. A system, comprising: a computed tomography (CT) scanner, at least one processor, and a memory storing instructions that, when executed by the at least one processor, cause the at least one processor to:

send an initial signal to the CT scanner to cause the CT scanner to acquire initial CT data of a heart of a patient during an initial acquisition window, the initial acquisition window being a length of time equal to one or more cardiac cycles of the heart of the patient;

receive the initial CT data from the CT scanner;

generate a four-dimensional (4D) CT image from the initial CT data;

determine, based on the 4D CT image, mechanical movement of a myocardium of the heart during the initial acquisition window;

identify, based on the mechanical movement of the myocardium of the heart during the initial acquisition window, an initial timeframe during the initial acquisition window when the myocardium of the heart is in a target position;

predict, based on the mechanical movement of the myocardium of the heart during the initial acquisition window and the initial timeframe within the initial acquisition window when the myocardium of the heart is in the target position, a plurality of subsequent timeframes when the myocardium of the heart will be in the target position, wherein the plurality of subsequent timeframes are updated in real time; and send a subsequent signal to the CT scanner to cause the CT scanner to acquire subsequent CT data at the plurality of subsequent timeframes.

13. The system of claim 12, wherein the initial acquisition window is 0.5-10 seconds.

14. The system of claim 12, wherein the instructions, when executed by the at least one processor, further cause the at least one processor to generate the 4D CT image from the initial CT data in real time.

15. The system of claim 12, wherein the instructions, when executed by the at least one processor, further cause the at least one processor to generate an alarm or notification at the system, to indicate when to administer coronary CTA (computed tomography angiography) contrast to the patient, wherein the alarm or notification is generated after sending the initial signal to the CT scanner and prior to sending the subsequent signal to the CT scanner.

16. The system of claim 12, wherein the instructions, when executed by the at least one processor, further cause the at least one processor to:

receive the subsequent CT data; and generate a 3D (three-dimensional) CT image from the subsequent CT data in real time.

17. The system of claim 16, wherein the instructions, when executed by the at least one processor, further cause the at least one processor to:

train a machine-learning model to predict the plurality of subsequent timeframes when the myocardium of the heart will be in the target position using the mechanical movement of the myocardium of the heart during the initial acquisition window and the initial timeframe within the initial acquisition window when the myocardium of the heart is in the target position; and execute the trained machine-learning model to predict the plurality of subsequent timeframes when the myocardium of the heart will be in the target position.

18. The system of claim 17, wherein the instructions, when executed by the at least one processor, further cause the at least one processor to:

identify, based on the 3D CT image, a subsequent position of the myocardium of the heart of the patient in the 3D CT image;

determine, based on the 3D CT image, that the subsequent position of the myocardium of the heart is not equal to the target position of the myocardium of the heart; and when the subsequent position of the myocardium of the heart is not equal to the target position of the myocardium of the heart, retrain the trained machine-learning model using the 3D CT image and the subsequent position of the myocardium of the heart of the patient in the 3D CT image.

19. The system of claim 18, wherein the instructions, when executed by the at least one processor, further cause the at least one processor to:

identify, based on the 4D CT image, a heart arrhythmia of the patient, wherein training the machine-learning model to predict the at the plurality of subsequent timeframes further comprises using the heart arrhythmia of the patient.

20. The system of claim 12, wherein the subsequent CT data comprises CT images of a plurality of segments of the myocardium corresponding to a coronary artery tree of the heart, and wherein the instructions, when executed by the at least one processor, cause the at least one processor to send the subsequent signal to the CT scanner to acquire the CT images of each of the plurality of segments of the myocardium during the plurality of subsequent timeframes until an entirety of the coronary artery tree of the heart is imaged.

* * * * *